(«12») United States Patent
Shin (10) Patent No.: US 9,538,108 B2
(45) Date of Patent: Jan. 3, 2017

(54) ENDOSCOPE SYSTEM AND PIXEL CORRECTION METHOD

(71) Applicant: OLYMPUS CORPORATION, Tokyo (JP)

(72) Inventor: Hidetoshi Shin, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/138,287

(22) Filed: Apr. 26, 2016

(65) Prior Publication Data

US 2016/0241800 A1 Aug. 18, 2016

Related U.S. Application Data

(63) Continuation of application No. PCT/JP2014/076949, filed on Oct. 8, 2014.

(30) Foreign Application Priority Data

Dec. 25, 2013 (JP) ................................. 2013-268103

(51) Int. Cl.
*H04N 5/00* (2011.01)
*H04N 5/367* (2011.01)
(Continued)

(52) U.S. Cl.
CPC ........... *H04N 5/367* (2013.01); *A61B 1/00006* (2013.01); *A61B 1/00009* (2013.01);
(Continued)

(58) Field of Classification Search
CPC ........ H04N 5/367; A61B 1/00006; A61B 1/05
(Continued)

(56) References Cited

U.S. PATENT DOCUMENTS

2004/0169747 A1* 9/2004 Ono ....................... H04N 9/045
348/272
2006/0017826 A1 1/2006 Sekimoto et al.
(Continued)

FOREIGN PATENT DOCUMENTS

JP 2006-026234 A 2/2006
JP 2010-028487 A 2/2010
(Continued)

OTHER PUBLICATIONS

International Search Report dated Jan. 13, 2015 issued in PCT/JP2014/076949.

(Continued)

*Primary Examiner* — Jeffery Williams
(74) *Attorney, Agent, or Firm* — Scully, Scott, Murphy & Presser, P.C.

(57) ABSTRACT

An endoscope system includes: a light source; an image sensor having pixels, each performing photoelectric conversion on received light to output an electric signal, and the image sensor imaging a subject to generate image data of the subject; a difference calculation unit that calculates, for each pixel, difference data between a dark image and a dark reference image, the dark image being output from the image sensor during lights-out time when the light source is turned off, and the dark reference image having been preliminarily obtained by averaging dark images generated by the image sensor; a detection unit that detects in the difference data a pixel whose pixel value is a threshold or more, as a blinking defective pixel in the image sensor; and a correction unit that corrects the electric signal output from the blinking defective pixel, using electric signals output from neighboring pixels of the blinking defective pixel.

7 Claims, 10 Drawing Sheets

(51) Int. Cl.
*G02B 23/24* (2006.01)
*A61B 1/00* (2006.01)
*A61B 1/05* (2006.01)
*A61B 1/07* (2006.01)
*H04N 5/217* (2011.01)
*H04N 5/235* (2006.01)

(52) U.S. Cl.
CPC .................. *A61B 1/05* (2013.01); *A61B 1/07* (2013.01); *G02B 23/2484* (2013.01); *H04N 5/2173* (2013.01); *H04N 5/2354* (2013.01)

(58) Field of Classification Search
USPC .......................................................... 348/68
See application file for complete search history.

(56) References Cited

U.S. PATENT DOCUMENTS

2007/0146508 A1* 6/2007 Oshima .................. H04N 5/361
348/243
2008/0122925 A1 5/2008 Sekimoto et al.
2010/0013964 A1 1/2010 Negishi
2013/0182934 A1* 7/2013 Topfer ..................... G06K 9/38
382/132

FOREIGN PATENT DOCUMENTS

| | | |
|---|---|---|
| JP | 2010-028488 A | 2/2010 |
| JP | 2013-207611 A | 10/2013 |
| JP | 2013-211785 A | 10/2013 |
| JP | 2014-216775 A | 11/2014 |

OTHER PUBLICATIONS

Japanese Office Action dated Dec. 15, 2015 issued in JP 2015-532203.
Japanese Office Action dated Sep. 24, 2015 issued in JP 2015-532203.

* cited by examiner

ENDOSCOPE SYSTEM AND PIXEL CORRECTION METHOD

CROSS-REFERENCE TO RELATED APPLICATIONS

This application is a continuation of PCT international application Ser. No. PCT/JP2014/076949 filed on Oct. 8, 2014 which designates the United States, incorporated herein by reference, and which claims the benefit of priority from Japanese Patent Application No. 2013-268103, filed on Dec. 25, 2013, incorporated herein by reference.

BACKGROUND

1. Technical Field

The disclosure relates to an endoscope system configured to be introduced into a living body to capture an image inside the living body, and a pixel correction method for correcting a pixel of an image sensor provided at the endoscope system.

2. Related Art

In the related art, a solid state image sensor such as a charge coupled device (CCD) and a complementary metal oxide semiconductor (CMOS) is formed of a plurality of pixels that outputs electric signals by receiving light and photoelectrically converting the light. In this kind of solid state image sensor, it is known that there may be a defective pixel that outputs an abnormal electric signal not associated with a receiving amount of the light. Kinds of such defective pixels may include: a constant defective pixel that constantly outputs an abnormal electric signal due to dust adhesion to a light receiving surface, a device crystal defect, and the like; and a blinking defective pixel that irregularly outputs an abnormal electric signal due to noise of a random telegraph signal (RTS) generated by current disorder caused by a fact that electrons moving inside a MOS transistor are captured by a trap level existing in a gate insulator film due to miniaturization of the solid state image sensor.

The blinking defective pixel appears on a captured image as image noise irregularly generated while a moving image is photographed. As a technology to remove such image noise, there is a known technology in which the solid state image sensor is made to capture images a plurality of times in a state that an image sensor is blocked from the light, and a blinking defective pixel is detected from a plurality of captured images, and then an electric signal of the detected blinking defective pixel is corrected (refer to Japanese Laid-open Patent Publication No. 2013-211785).

SUMMARY

In some embodiments, an endoscope system includes: a light source unit configured to emit illumination light to illuminate a subject; an image sensor having a plurality of pixels arranged two-dimensionally, each of the plurality of pixels being configured to receive light and perform photoelectric conversion on the received light to output an electric signal, and the image sensor being configured to image the subject at a predetermined frame rate and generate image data of the subject; an illumination controller configured to turn off the light source unit in a predetermined cycle; a difference calculation unit configured to calculate, for each pixel, difference data between a dark image and a dark reference image, the dark image being output from the image sensor during lights-out time when the illumination controller turns off the light source unit, and the dark reference image having been obtained by averaging a plurality of dark images generated by the image sensor and having been preliminarily recorded; a blinking defective pixel detection unit configured to determine, for each pixel of the difference data calculated by the difference calculation unit, whether a pixel value is a predetermined threshold value or more, and to detect a pixel whose pixel value is the predetermined threshold value or more, as a blinking defective pixel in the image sensor; an image output timing adjustment unit configured to temporarily hold the image data generated by the image sensor, and to output the image data at predetermined timing; and a pixel correction unit configured to correct the electric signal output from the blinking defective pixel detected by the blinking defective pixel detection unit in the image data output by the image output timing adjustment unit, by using electric signals output from neighboring pixels of the blinking defective pixel, and to output the image data to a display device. If the illumination controller turns off the light source unit n times ($n \geq 1$) per unit time and the predetermined frame rate is set to N, the illumination controller is configured to turn off the light source unit such that the lights-out time of the light source unit per frame is 1/N, and the image output timing adjustment unit is configured to output the image data at a frame rate of N−n.

In some embodiments, a pixel correction method executed by an endoscope system is provided. The endoscope system includes: a light source unit configured to emit illumination light to illuminate a subject; and an image sensor having a plurality of pixels arranged two-dimensionally, each of the plurality of pixels being configured to receive light and perform photoelectric conversion on the received light to output an electric signal. The method includes: turning off the light source unit in a predetermined cycle; causing the image sensor to perform imaging during lights-out time when the light source unit is turned off to generate a dark image; calculating, for each pixel, difference data between the dark image and a dark reference image, the dark reference image having been obtained by averaging a plurality of dark images generated by the image sensor and having been preliminarily recorded; determining, for each pixel of the difference data, whether a pixel value is a predetermined threshold value or more, and detecting a pixel whose pixel value is the predetermined threshold value or more, as a blinking defective pixel in the image sensor; causing the image sensor to image the subject at a predetermined frame rate to generate image data of the subject; temporarily holding the image data, and outputting the image data at predetermined timing; and correcting the electric signal output from the blinking defective pixel in the image data output at the predetermined timing, by using electric signals output from neighboring pixels of the blinking defective pixel, and outputting the image data to a display device. If the light source unit is turned off n times ($n \geq 1$) per unit time and the predetermined frame rate is set to N, the light source unit is turned off such that the lights-out time of the light source unit per frame is 1/N, and the image data is output at a frame rate of N−n.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the present invention (hereinafter referred to as "embodiment(s)"), reference will be made below to an exemplary medical endoscope system adapted to capture and display an image inside a body cavity of a subject such as a patient. Note that the present invention is not limited by the embodiments. The same reference signs are used to designate the same elements throughout the drawings. The drawings are provided as schematic illustrations and a relationship between a thickness and a width of each of members, a proportion of each of the member, and the like are different from those in practice. Additionally, between the drawings, portions having dimensions and ratios different from one another are also included.

First Embodiment

Figure 1:
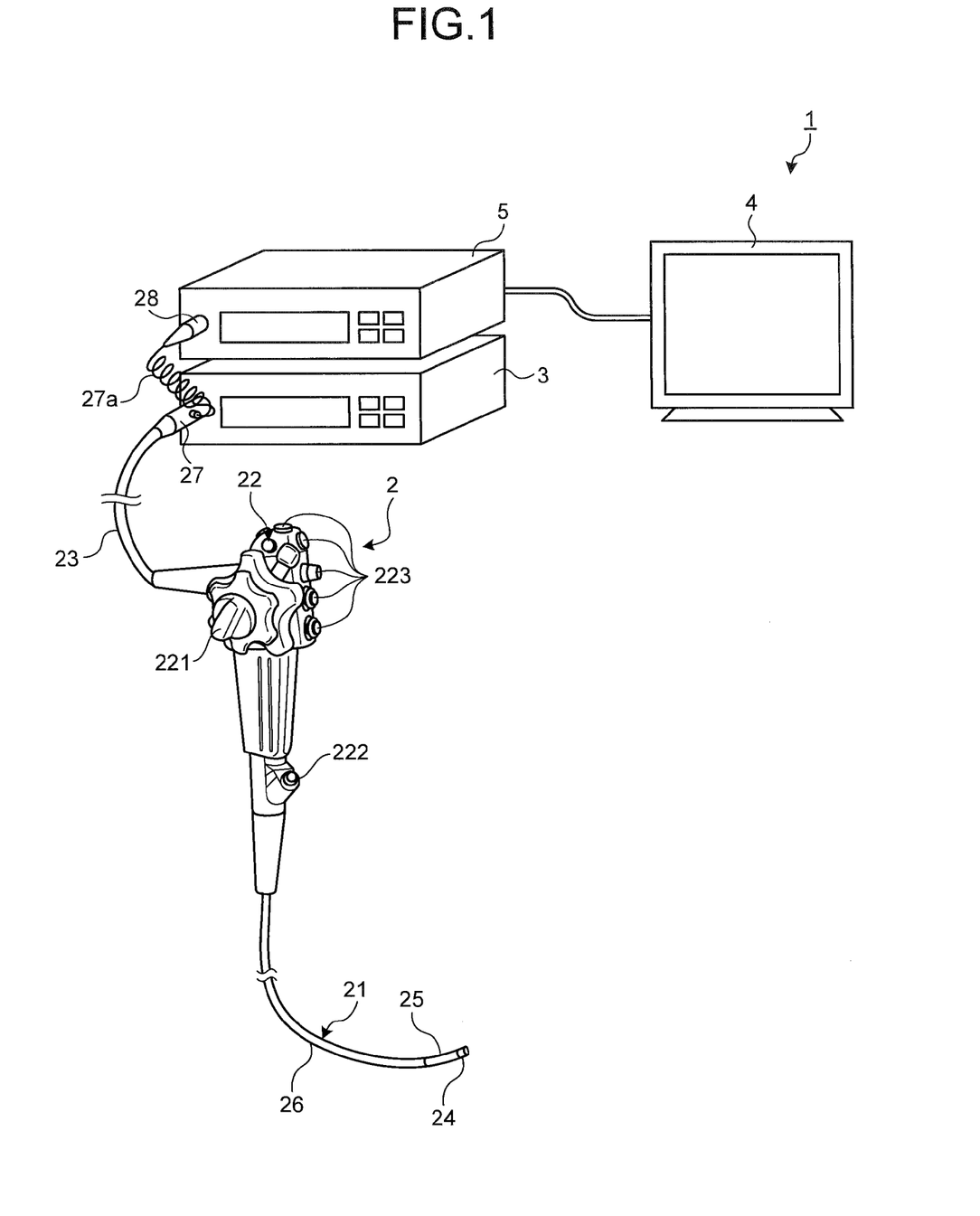
FIG. 1 is a diagram illustrating a brief structure of an endoscope system according to a first embodiment of the present invention.
Figure 2:
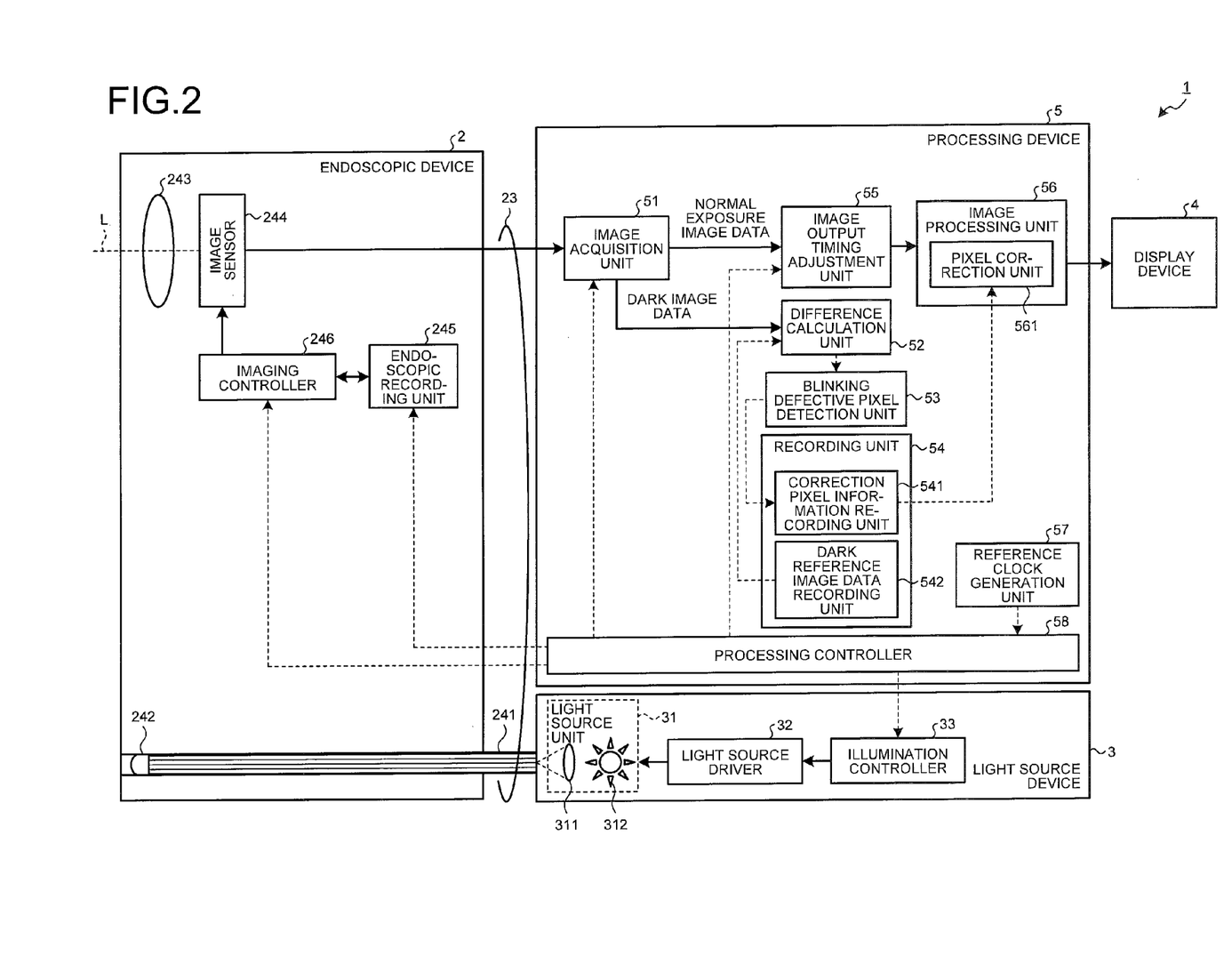
FIG. 2 is a block diagram illustrating a functional configuration of a main portion of the endoscope system according to the first embodiment of the present invention.

FIG. 1 is a diagram illustrating a brief structure of an endoscope system according to a first embodiment of the present invention. FIG. 2 is a block diagram illustrating a functional configuration of a main portion of the endoscope system according to the first embodiment of the present invention.

An endoscope system 1 illustrated in FIGS. 1 and 2 includes an endoscopic device 2 (electronic scope) that captures an in-vivo image of a subject by inserting a distal end portion of the endoscopic device into a body cavity of the subject; a light source device 3 that generates illumination light to illuminate an object from the distal end of the endoscopic device 2; a display device 4 that can display the in-vivo image captured by the endoscopic device 2; and a processing device 5 (external processor) that applies predetermined image processing to the in-vivo image captured by the endoscopic device 2, outputs the same to the display device 4, and further integrally controls operation of the entire endoscope system 1.

First, a configuration of the endoscopic device 2 will be described.

The endoscopic device 2 includes: an insertion portion 21 having flexibility and formed in a thin long shape; an operating unit 22 connected to a proximal end side of the insertion portion 21 and adapted to receive various kinds of operation signal input; and a universal cord 23 extending from the operating unit 22 in a direction different from an extending direction of the insertion portion 21, and incorporating various kinds of cables to connect the light source device 3 and the processing device 5.

The insertion portion 21 includes: a distal end portion 24 incorporating an image sensor described later; a bending portion 25 formed of a plurality of bending pieces and capable of being freely bent; and a flexible tube portion 26 connected to a proximal end side of the bending portion 25, having flexibility, and formed in a long shape.

The distal end portion 24 includes: a light guide 241 formed by using glass fibers and the like and constituting a light guide passage for the light emitted from the light source device 3; an illumination lens 242 provided at a distal end of the light guide 241; an optical system 243 for light condensing; an image sensor 244 disposed at an image forming position of the optical system 243 and having a plurality of pixels two-dimensionally arrayed and adapted to photoelectrically convert, to an electric signal, the light condensed by the optical system 243; an endoscopic recording unit 245 that records various kinds of information related to the endoscopic device 2; and an imaging controller 246 that controls the image sensor 244.

The optical system 243 is formed by using one or plurality of lenses and moved along an apical axis L, thereby performing optical zooming to change a viewing angle and changing a focal point.

The image sensor 244 has the plurality of pixels that is two-dimensionally arrayed and outputs an electric signal by receiving light and photoelectrically converting the light, and the image sensor captures an image of the object (body cavity) at a predetermined frame rate and outputs image data of the object. More specifically, the image sensor 244 is formed by using an image sensor such as a charge coupled device (CCD) or a complementary metal oxide semiconductor (CMOS) in which a plurality of pixels is arrayed in a two-dimensional matrix, and each of the pixels includes: a photodiode to accumulate electric charge corresponding to a light amount; and an amplifier to amplify the electric charge accumulated by the photodiode. The image sensor 244 outputs the electric signal generated by each of the pixels as image data (RAW data) to the processing device 5.

The endoscopic recording unit 245 records various kinds of information related to the endoscopic device 2 such as identification information to identify the endoscopic device 2 and identification information of the image sensor 244. The endoscopic recording unit 245 is formed by using a non-volatile memory and the like.

The imaging controller 246 controls operation of the image sensor 244 based on command information received from the processing device 5. More specifically, the imaging controller 246 controls a frame rate of the image sensor 244 based on the command information received from the processing device 5. For example, the imaging controller 246 controls the image sensor 244 to output image data at 60 fps.

The operating unit 22 includes: a bending knob 221 to bend the bending portion 25 in a vertical direction and a horizontal direction; a treatment tool insertion portion 222 to insert a treatment tool, such as a living body forceps, a laser scalpel, or a TEST probe, into a body cavity; and a plurality of switches 223, namely, an operation input unit to input operation command signals for peripheral apparatuses such as an air feeding means, a water feeding means, and a gas feeding means in addition to the light source device 3 and processing device 5. A treatment tool inserted from the treatment tool insertion portion 222 is passed through a treatment instrument channel (not illustrated) at the distal end portion 24, and comes out from an opening (not illustrated).

The universal cord 23 incorporates at least the light guide 241 and a cable assembly formed by assembling one or a plurality of cables. The cable assembly includes signal lines through which signals are transmitted and received between the endoscopic device 2, light source device 3, and processing device 5. Examples of the signal lines include a signal line for transmitting and receiving setting data, a signal line for transmitting and receiving an image signal, and a signal line for transmitting and receiving a drive timing signal to drive the image sensor 244. The universal cord 23 includes a connector portion 27 detachably attached to the light source device 3. The connector portion 27 is provided with a coil cable 27a having a coil shape in an extending manner. At an extending end of the coil cable 27a, a connector portion 28 detachably attached to the processing device 5 is provided.

Next, a configuration of the light source device 3 will be described.

The light source device 3 includes a light source unit 31, a light source driver 32, and an illumination controller 33.

The light source unit 31 emits illumination light to illuminate a subject. The light source unit 31 includes a condenser lens 311 and a light source 312. The condenser lens 311 is formed by using one or a plurality of lenses and condenses light emitted from the light source 312. The light source 312 is formed by using a light emitting diode (LED) and generates white light. Note that the light source 312 may also be formed by using a red LED, a green LED, and a blue LED, and may generate white light by simultaneously emitting the respective LEDs.

The light source driver 32 intermittently causes the light source 312 to generate white light by supplying the light source 312 with electricity under control of the illumination controller 33. The light emitted from the light source 312 is emitted from a distal end of the distal end portion 24 via the condenser lens 311 and the light guide 241.

The illumination controller 33 controls lighting timing of the light source 312 based on a command signal received from the processing device 5. Specifically, the illumination controller 33 turns off the light source 312 in a predetermined cycle. More specifically, in the case where the illumination controller 33 turns off the light source unit 31 n times (n≥1) per unit time and further a frame rate of image data generated by the image sensor 244 is N, the illumination controller 33 also turns off the light source unit 31 by setting a lights-out time of the light source unit 31 to 1/N. For example, in the case where the frame rate of the image data generated by the image sensor 244 is 61 fps, the illumination controller 33 turns off the light source 312 during one frame only and further turns off the light source unit 31 by setting the lights-out time to $1/61$ (sec). The illumination controller 33 is formed by using a CPU or the like.

Next, a configuration of the display device 4 will be described.

The display device 4 displays an in-vivo image received from the processing device 5. Further, the display device 4 displays the various kinds of information related to the endoscope system 1. The display device 4 is formed by using a liquid crystal, an organic electro luminescence (EL) or the like.

Next, a configuration of the processing device 5 will be described.

The processing device 5 includes an image acquisition unit 51, a difference calculation unit 52, a blinking defective pixel detection unit 53, a recording unit 54, an image output timing adjustment unit 55, an image processing unit 56, a reference clock generation unit 57, and a processing controller 58.

The image acquisition unit 51 acquires image data generated by the image sensor 244. More specifically, the image acquisition unit 51 acquires the image data from the image sensor 244 at a predetermined frame rate under the control of the processing controller 58. Further, in the case where the image data acquired from the image sensor 244 under the control of the processing controller 58 is normal exposure image data captured under normal exposure, the image acquisition unit 51 outputs the image data to the image output timing adjustment unit 55. On the other hand, in the case where the image data acquired from the image sensor 244 is dark image data, the image acquisition unit 51 outputs the dark image data to the difference calculation unit 52.

The difference calculation unit 52 calculates difference data (difference value) between a dark image corresponding to the dark image data received from the image acquisition unit 51 and a dark reference image corresponding to dark reference image data recorded in a later-described dark reference image data recording unit 542 of the recording unit 54, and outputs a calculation result thereof to the blinking defective pixel detection unit 53. More specifically, the difference calculation unit 52 calculates difference data of a pixel value (electric signal) per pixel between the dark image and the dark reference image, and outputs the calculation result to the blinking defective pixel detection unit 53.

The blinking defective pixel detection unit 53 detects a blinking defective pixel in the image sensor 244 based on the difference data received from the difference calculation unit 52. More specifically, the blinking defective pixel detection unit 53 determines whether a pixel value is a predetermined threshold value or more as for the difference data per pixel received from the difference calculation unit 52, and detects a pixel having the pixel value of the predetermined threshold value or more as a blinking defective pixel. The blinking defective pixel detection unit 53 outputs, to a correction pixel information recording unit 541, positional information (pixel address) of the detected blinking defective pixel on the image sensor 244.

The recording unit 54 records various kinds of programs to operate the endoscope system 1, various kinds of parameters and the like needed in operation of the endoscope system 1. Further, the recording unit 54 includes: the correction pixel information recording unit 541 to record positional information of a defective pixel and positional information of a blinking defective pixel in the image sensor 244; and a dark reference image data recording unit 542 to record the dark reference image data used at the time of detecting the blinking defective pixel. The dark reference image data is obtained by averaging a plurality of dark image data before shipment of the endoscopic device 2 or at the time of starting operation of the endoscope system 1. In this dark reference image data, defective pixel information is included. The recording unit 54 is formed by using a recording medium such as a synchronous dynamic random access memory (SDRAM), a flash memory, or the like, and a hard disk drive (HDD).

The image output timing adjustment unit 55 temporarily holds normal image data received from the image acquisition unit 51 and outputs the normal image data to the image processing unit 56 at predetermined timing under the control of the processing controller 58. More specifically, in the case where the frame rate of the image data generated by the image sensor 244 is N, the image output timing adjustment unit 55 executes outputting by setting a frame rate to N−n when the normal image data received from the image sensor 244 via the image acquisition unit 51 is output to the image processing unit 56. For example, when lights-out of the light source unit 31 is once (n=1) in the case where the frame rate of the image data of the image sensor 244 is 61 fps, the image output timing adjustment unit 55 outputs the normal image data sequentially received from the image sensor 244 to the image processing unit 56 at 60 fps via the image acquisition unit 51.

The image processing unit 56 applies various kinds of image processing to the image data received from the image output timing adjustment unit 55, and outputs the image data to the display device 4. More specifically, the image processing unit 56 applies, to the image data, at least image processing including such as optical black (OB) subtraction processing to correct black output, white balance (WB) adjustment processing to adjust color tone of the image data, color matrix operation processing, gamma correction processing, color reproduction processing, and edge enhancement processing. Further, the image processing unit 56 includes a pixel correction unit 561.

The pixel correction unit 561 performs correction processing to correct respective electric signals of a defective pixel and a blinking defective pixel by using electric signals of neighboring pixels and adjacent pixels of the defective pixel and the blinking defective pixel based on defective pixel information and blinking defective pixel information recorded in the correction pixel information recording unit 541 of the recording unit 54.

The reference clock generation unit 57 generates a reference clock signal to be reference of operation in each of the units in the endoscope system 1, and supplies the generated reference clock signal to each of the units in the endoscope system 1.

The processing controller 58 executes: drive control for each of the units including the endoscopic device 2 and the light source device 3; and input/output control for information relative to each of the units. The processing controller 58 is formed by using a CPU and the like.

Figure 3:
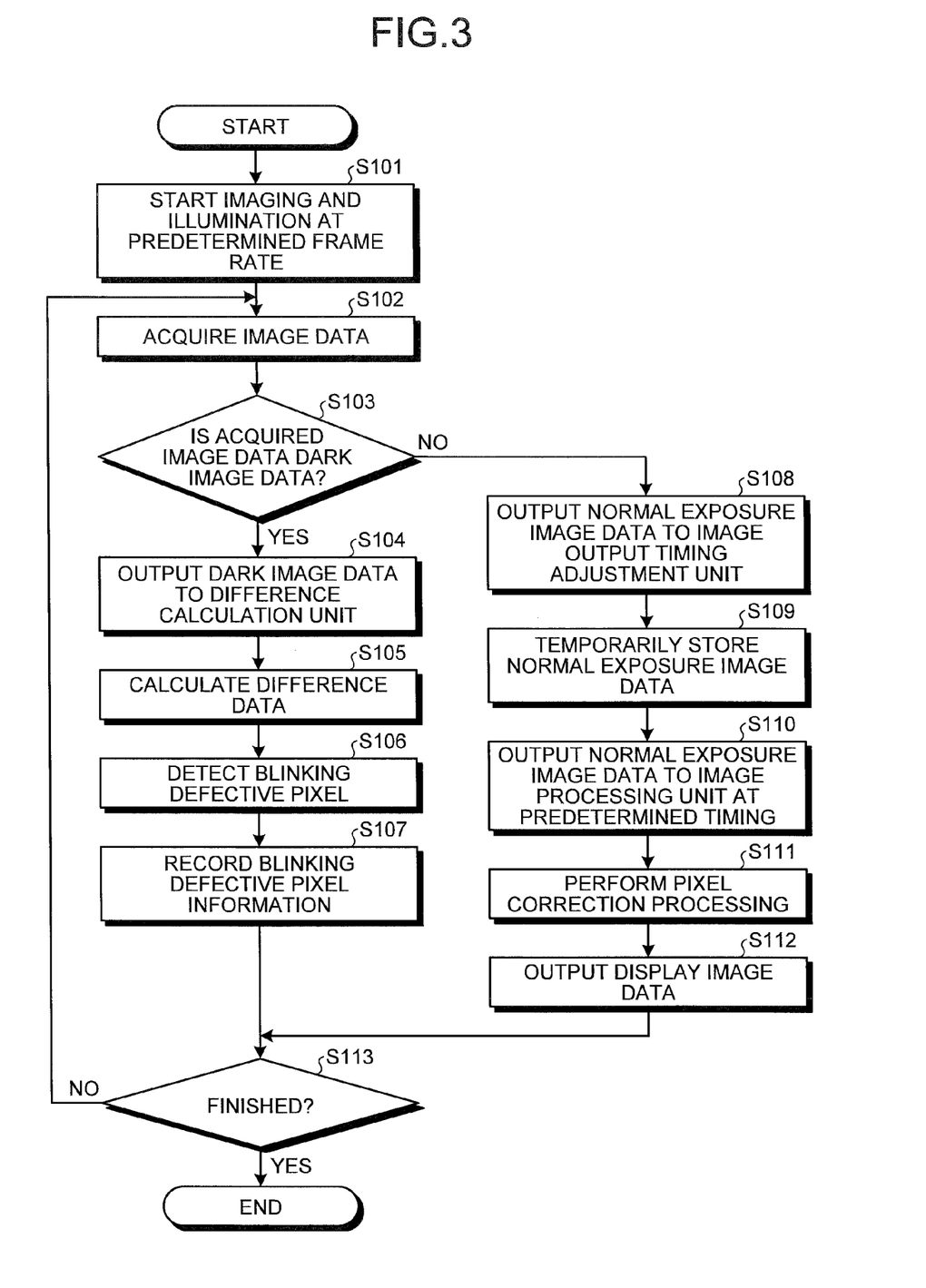
FIG. 3 is a flowchart illustrating an outline of processing executed by the endoscope system according to the first embodiment of the present invention.

The processing executed by the endoscope system 1 having the above-described configuration will be described. FIG. 3 is a flowchart illustrating an outline of the processing executed by the endoscope system 1.

Figure 4:
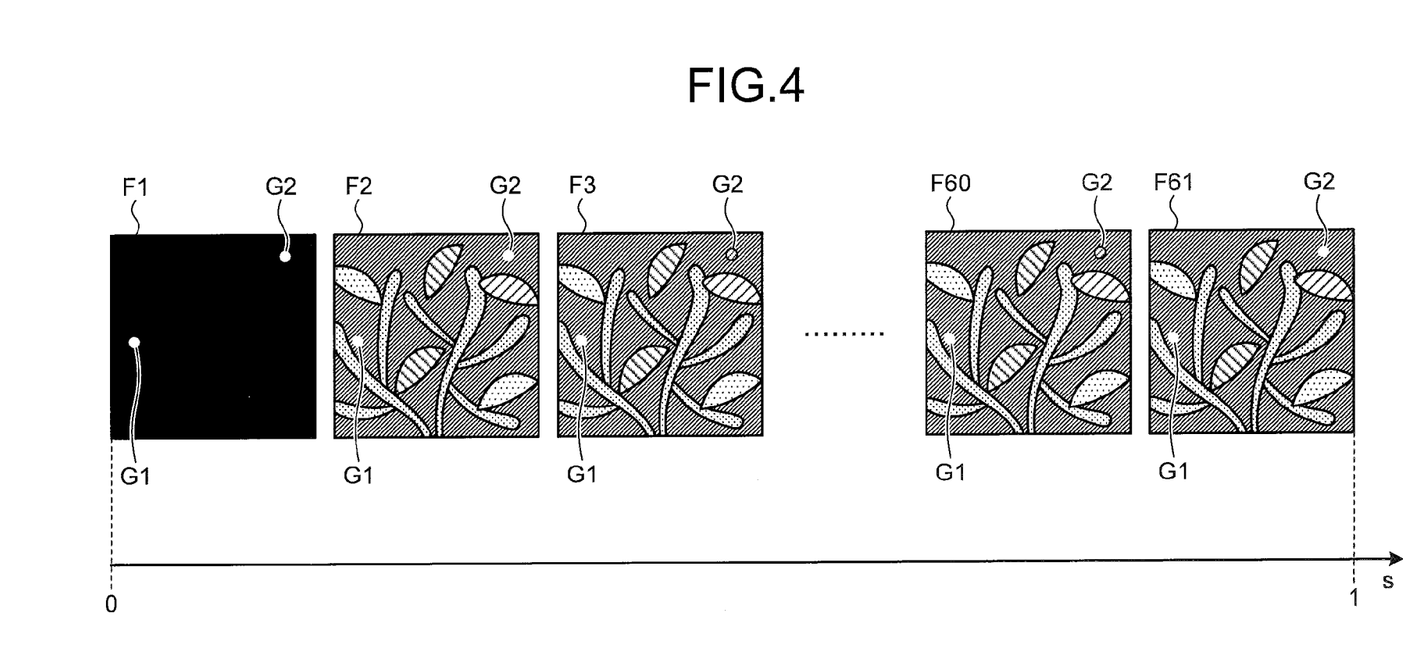
FIG. 4 is a diagram schematically illustrating an image corresponding to image data generated at a predetermined frame rate by an image sensor of the endoscope system according to the first embodiment of the present invention.

As illustrated in FIG. 3, in the endoscope system 1, the image sensor 244 starts imaging at a predetermined frame rate and further the light source device 3 starts illumination light emission in synchronization with the frame rate of the image sensor 244 (Step S101). More specifically, the imaging controller 246 makes the image sensor 244 start image capturing at the predetermined frame rate. For example, as illustrated in FIG. 4, the imaging controller 246 makes the image sensor 244 start image capturing inside a body cavity of a subject at 61 fps. Further, the illumination controller 33 turns off the light source 312 in a predetermined cycle in synchronization with the frame rate of the image sensor 244. For example, as illustrated in FIG. 4, in the case where the image sensor 244 captures and image of the inside of the body cavity of the subject at 61 fps, the illumination controller 33 turns off the light source 312 at the first frame. In this case, the image sensor 244 generates dark image data. Note that a pixel G1 indicates a defective pixel and a pixel G2 indicates a blinking defective pixel in each of images F1 to F61 in FIG. 4. Further, in the following, a case where the blinking defective pixel outputs a normal image signal is indicated by hatching, and a case of outputting an abnormal image signal is indicated by white space on a colored background. The case illustrated in FIG. 4 illustrates a state in which the blinking defective pixels G2 are generated on a dark image F1 in the first frame, a normal exposure image F2 in the second frame, and a normal exposure image F61 in the $61^{th}$ frame.

Subsequently, the image acquisition unit 51 acquires image data generated by the image sensor 244 (Step S102).

After that, the processing controller 58 determines whether the image data acquired by the image acquisition unit 51 from the image sensor 244 is the dark image data (Step S103). More specifically, the processing controller 58 determines whether the image data acquired by the image acquisition unit 51 from the image sensor 244 is the image data generated by the image sensor 244 during the lights-out time when the light source 312 is turned off by the illumination controller 33. In the case where the processing controller 58 determines that the image data acquired by the image acquisition unit 51 from the image sensor 244 is the dark image data (Step S103: Yes), the endoscope system 1 proceeds to Step S104 described later. In contrast, in the case where the processing controller 58 determines that the image data acquired by the image acquisition unit 51 from the image sensor 244 is not the dark image data (Step S103: No), the endoscope system 1 proceeds to Step S108 described later.

In Step S104, the processing controller 58 controls the dark image data acquired by the image acquisition unit 51 from the image sensor 244 to be output to the difference calculation unit 52.

Subsequently, the difference calculation unit 52 calculates the difference data based on the dark image corresponding to the dark image data received from the image acquisition unit 51 and the dark reference image corresponding to the dark reference image data recorded in the dark reference image data recording unit 542 (Step S105).

Figure 5:
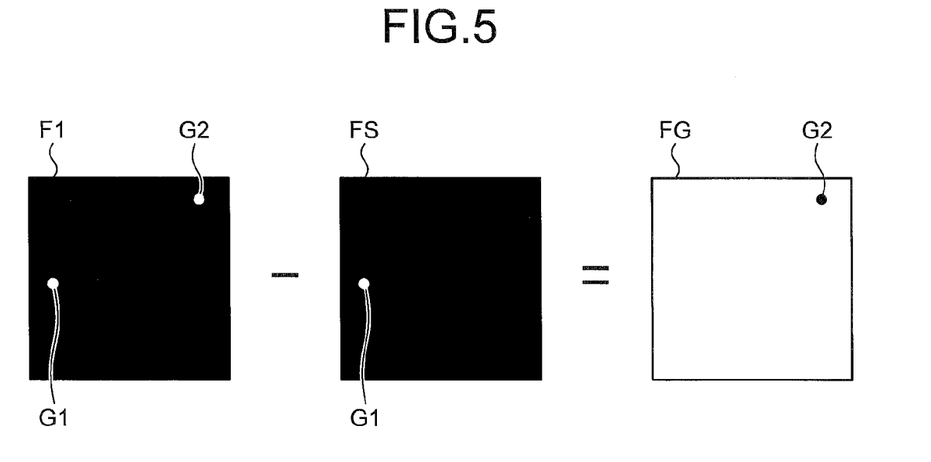
FIG. 5 is a diagram schematically illustrating difference data calculated by a difference calculation unit of the endoscope system according to the first embodiment of the present invention.

FIG. 5 is a schematic diagram to describe a calculation method of the difference data calculated by the difference calculation unit 52. As illustrated in FIG. 5, the difference calculation unit 52 calculates, per pixel, difference data FG of a pixel value (image signal) between a dark image F1 and a dark reference image FS by subtracting the dark reference image FS from the dark image F1. Note that pixel value of the blinking defective pixel G2 is indicated by a black circle for clarification in FIG. 5.

After Step S105, the blinking defective pixel detection unit 53 detects a blinking defective pixel in the image sensor 244 based on the difference data calculated by the difference calculation unit 52 (Step S106). More specifically, the blinking defective pixel detection unit 53 determines whether the pixel value of the difference data calculated per pixel by the difference calculation unit 52 exceeds a predetermined threshold value, and detects a pixel exceeding the predetermined threshold value as a blinking defective pixel to be corrected. For example, in the case illustrated in FIG. 5, the blinking defective pixel detection unit 53 detects the blinking defective pixel G2 of the difference data FG.

Subsequently, the processing controller 58 records, in the correction pixel information recording unit 541, the blinking defective pixel information related to a position of the blinking defective pixel in the image sensor 244 detected by the blinking defective pixel detection unit 53 (Step S107). After Step S107, the endoscope system 1 proceeds to Step S113 described later.

In Step S108, the processing controller 58 outputs, to the image output timing adjustment unit 55, the normal exposure image data acquired by the image acquisition unit 51 from the image sensor 244.

Subsequently, the image output timing adjustment unit 55 temporarily stores (holds) the normal exposure image data received from the image acquisition unit 51 (Step S109).

After that, the image output timing adjustment unit 55 outputs the normal exposure image data to the image processing unit 56 at the predetermined timing (Step S110). More specifically, the image output timing adjustment unit 55 outputs the normal exposure image data to the image processing unit 56 at a frame rate so as to be the same frame rate of the image data generated by the image sensor 244 per unit time. For example, the image output timing adjustment unit 55 outputs the normal exposure image data to the image processing unit 56 at 60 fps.

Figure 6:
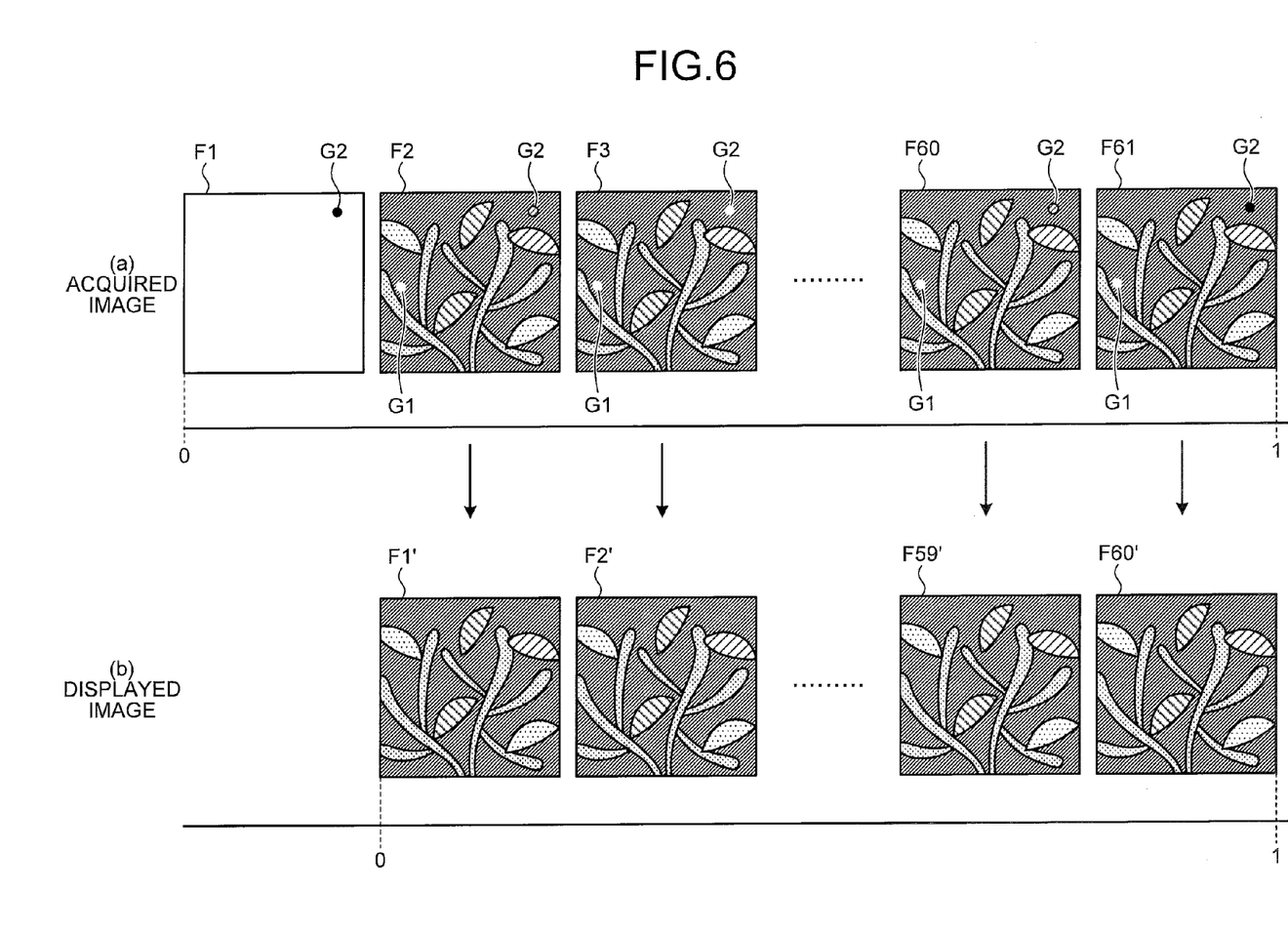
FIG. 6 is a diagram schematically illustrating an image corresponding to image data subjected to pixel correction executed by a pixel correction unit of the endoscope system according to the first embodiment of the present invention.

Subsequently, the pixel correction unit 561 applies the pixel correction processing by using the electric signals of neighboring pixels to each of the defective pixel and the blinking defective pixel in the normal exposure image corresponding to the normal exposure image data received from the image output timing adjustment unit 55 based on the defective pixel information and the blinking defective pixel information recorded in the correction pixel information recording unit 541 (Step S111). More specifically, the pixel correction unit 561 corrects, as illustrated in FIG. 6, the defective pixels G1 and the blinking defective pixels G2 in the normal exposure images F2 to F61 sequentially received from the image output timing adjustment unit 55 by using the electric signals of the neighboring pixels of the defective pixel G1, for example, four pixels adjacent to the defective pixel G1 based on the defective pixel information and the defective pixel information recorded in the correction pixel information recording unit 541. Further, the pixel correction unit 561 corrects the blinking defective pixel G2 by using the electric signals of the adjacent pixels of the blinking defective pixel G2. Then, display images F1' to F60' corresponding to display image data are generated (FIG. 6(a) →FIG. 6(b)). In this case, the image processing unit 56 applies, to the normal exposure image data, basic image processing needed to develop the above-described normal exposure image data.

After that, the image processing unit 56 outputs the display image data to the display device 4 (Step S112). By this, as illustrated in FIG. 6(b), the display device 4 can sequentially display the display images F1' to F60' in which the pixels of the defective pixel G1 and the blinking defective pixel G2 are corrected, and high-resolution image can be displayed. After Step S112, the endoscope system 1 proceeds to Step S113.

In the case where a command signal to finish image capturing inside the body cavity of the subject by endoscope system 1 is received from the switch 223 after Step S107 or after Step S112 (Step S113: Yes), the endoscope system 1 finishes the processing. On the other and, in the case where the command signal to finish image capturing inside the body cavity of the subject by endoscope system 1 is not received from the switch 223 (Step S113: No), the endoscope system 1 returns to Step S102.

According to the above-described first embodiment of the present invention, high-resolution image can be displayed because the blinking defective pixel in the image sensor 244 can be surely detected and corrected.

Second Embodiment

Next, a second embodiment of the present invention will be described. In a first embodiment described above, dark reference image data is recorded in a dark reference image data recording unit 542, but in the second embodiment, dark reference image data is generated while examining a subject or before examining a subject. More specifically, in the second embodiment, a light source unit is turned off in a predetermined cycle. Further, in the second embodiment, the dark reference image data is generated by: sequentially recording a plurality of dark image data generated by an image sensor at lights-out time of the light source unit; and averaging an electric signal per pixel. Therefore, in the following, a configuration of an endoscope system according to the second embodiment will be described first, and then processing executed by the endoscope system according to the second embodiment will be described. Note that elements same as an endoscope system 1 according to the above-described first embodiment will be denoted by the same reference signs, and a description therefor will be omitted.

Figure 7:
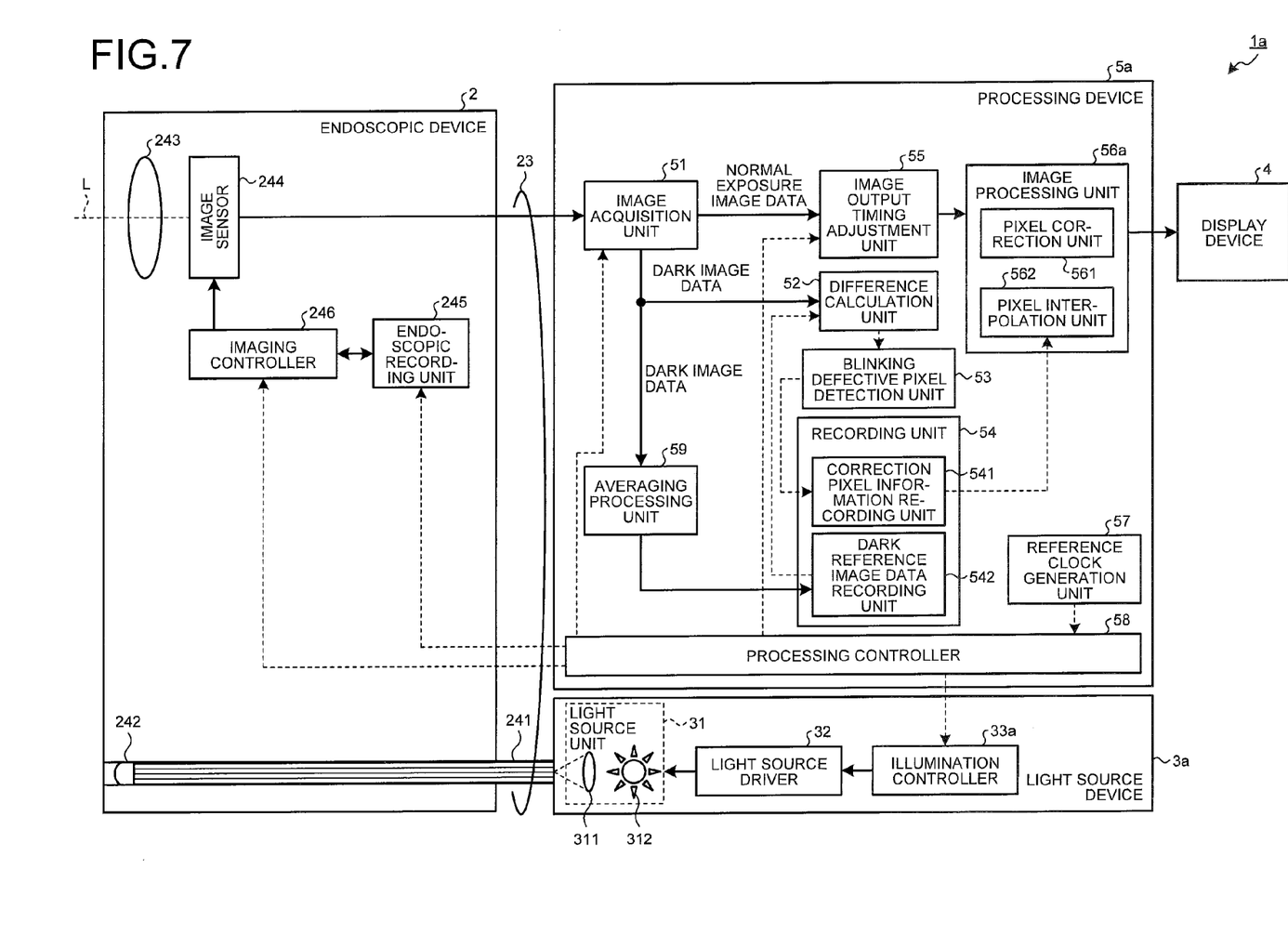
FIG. 7 is a block diagram illustrating a functional configuration of a main portion of an endoscope system according to a second embodiment of the present invention.

FIG. 7 is a block diagram illustrating functions of a main portion of the endoscope system according to the second embodiment of the present invention. An endoscope system 1a illustrated in FIG. 7 includes an endoscopic device 2, a light source device 3a, a display device 4, and a processing device 5a.

First, a configuration of the light source device 3a will be described.

The light source device 3a includes a light source unit 31, a light source driver 32, and an illumination controller 33a.

The illumination controller 33a turns off the light source unit 31 in a predetermined cycle in synchronization with a frame rate of image data generated by an image sensor 244. More specifically, in the case where the illumination controller 33a turns off the light source unit 31 n times (n≥1) per unit time and further a frame rate of image data generated by the image sensor 244 is N, the illumination controller 33a also turns off the light source unit 31 by setting lights-out time of the light source unit 31 to 1/N. For example, in the case where a frame rate of image data generated by the image sensor 244 is 60 fps, the illumination controller 33a turns off a light source 312 during respective imaging periods of 1 frame, 11 frame, 21 frame, 31 frame, 41 frame, and 51 frame. In this case, the illumination controller 33a turns off the light source unit 31 by setting the lights-out time of the light source unit 31 per frame to 1/60 (sec). Further, for example, in the case where the frame rate of the image data generated by the image sensor 244 is 120 fps, the illumination controller 33a may also turn off the light source unit 31 during imaging periods of even numbered frames or odd numbered frames.

Next, a configuration of the processing device 5a will be described.

The processing device 5a includes an image acquisition unit 51, a difference calculation unit 52, a blinking defective pixel detection unit 53, a recording unit 54, an image output timing adjustment unit 55, an image processing unit 56a, a reference clock generation unit 57, a processing controller 58, and an averaging processing unit 59.

The image processing unit 56a includes a pixel correction unit 561 and an image interpolation unit 562.

In the case where receiving timing of normal exposure image data received from the image output timing adjustment unit 55 corresponds to a frame of dark image data, the image interpolation unit 562 generates normal exposure image data corresponding to the frame of the dark image data based on most recent normal exposure image data and current normal exposure image data, and outputs the same to the display device 4.

The averaging processing unit 59 averages a plurality of dark image data sequentially received from the image acquisition unit 51 to generate the dark reference image data. More specifically, in the case where a distal end portion 24 of the endoscopic device 2 is inserted into a body cavity of a subject at the time of examining or while examining the subject, the averaging processing unit 59 generates the dark reference image data by averaging the plurality of dark image data sequentially received from the image acquisition unit 51. The averaging processing unit 59 outputs the dark reference image data to the dark reference image data recording unit 542, and sequentially updates the dark reference image data.

Figure 8:
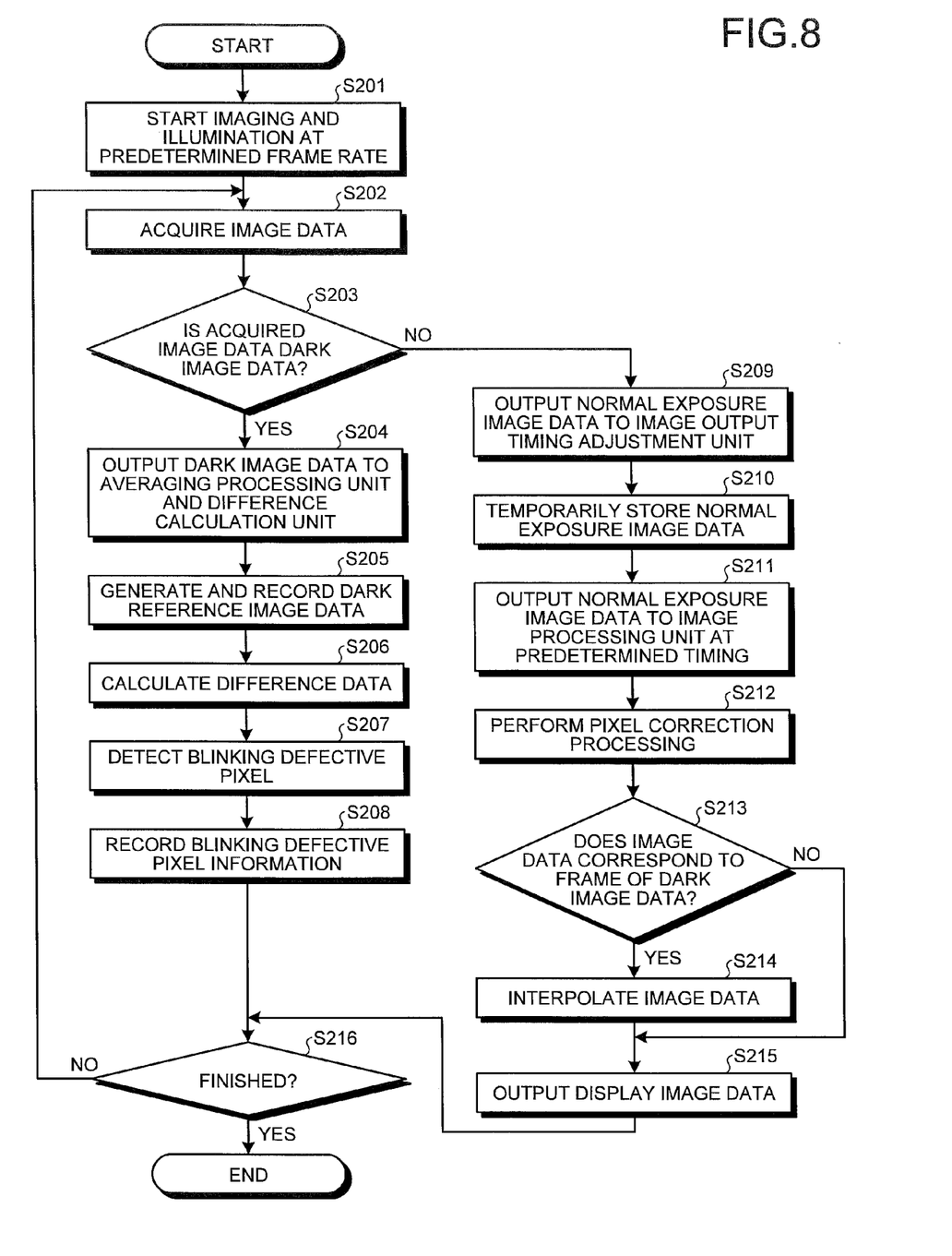
FIG. 8 is a flowchart illustrating an outline of processing executed by the endoscope system according to the second embodiment of the present invention.

The processing executed by the endoscope system 1a having the above-described configuration will be described. FIG. 8 is a flowchart illustrating an outline of the processing executed by the endoscope system 1a.

Steps S201 to S203 in FIG. 8 correspond to Steps S101 to S103 described above in FIG. 3 respectively.

In Step S204, the processing controller 58 outputs the dark image data acquired by the image acquisition unit 51 from the image sensor 244 to the difference calculation unit 52 and the averaging processing unit 59.

Figure 9:
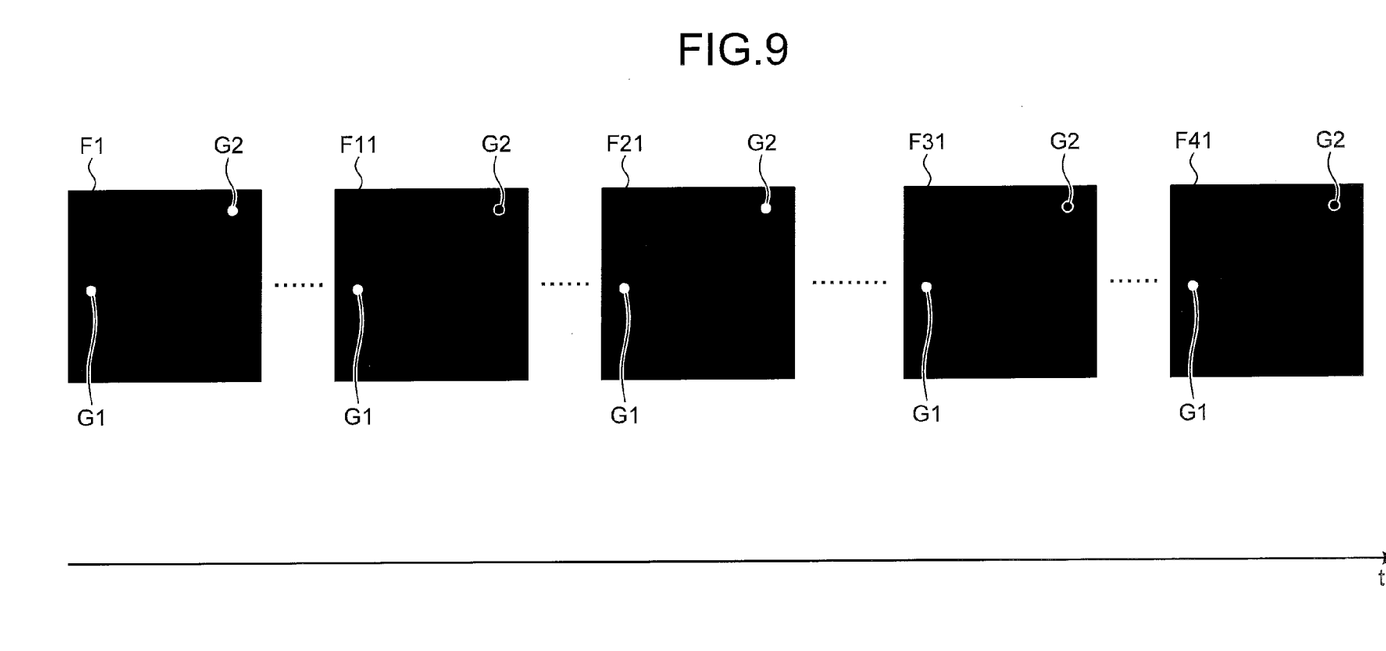
FIG. 9 is a diagram schematically illustrating an outline of a method of generating dark reference image data generated by an averaging processing unit of the endoscope system according to the second embodiment of the present invention.
Figure 10:
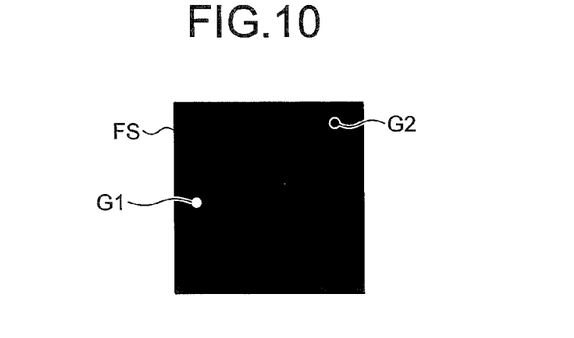
FIG. 10 is a diagram illustrating an exemplary dark reference image corresponding to the dark reference image data generated by the averaging processing unit of the endoscope system according to the second embodiment of the present invention.

Subsequently, the averaging processing unit 59 stores the dark image data received from the image acquisition unit 51, and generates the dark reference image data by averaging the plurality of stored dark reference image data, and then records the dark reference image data in the dark reference image data recording unit 542 (Step S205). More specifically, as illustrated in FIG. 9, the averaging processing unit 59 stores a plurality of dark images F1, F11, F21, F31, and F41 corresponding to the plurality of dark image data sequentially received from the image acquisition unit 51, and adds up pixel values (electric signals) of respective pixels in the plurality of stored dark images F1, F11, F21, F31, and F41, and then divides the added value by the number of dark images, thereby generating the dark reference image data. FIG. 10 is a diagram illustrating an exemplary dark reference image FS corresponding to the dark reference image data. In FIG. 9, the dark images F1, F11, F21, F31, and F41 are sequentially received, but normal exposure images corresponding to normal exposure image data are consecutively generated by the image sensor 244 between the dark image F1 and the F11, for example.

Steps S206 to S212 corresponds to Steps S105 to S111 described above in FIG. 3 respectively.

Figure 11:
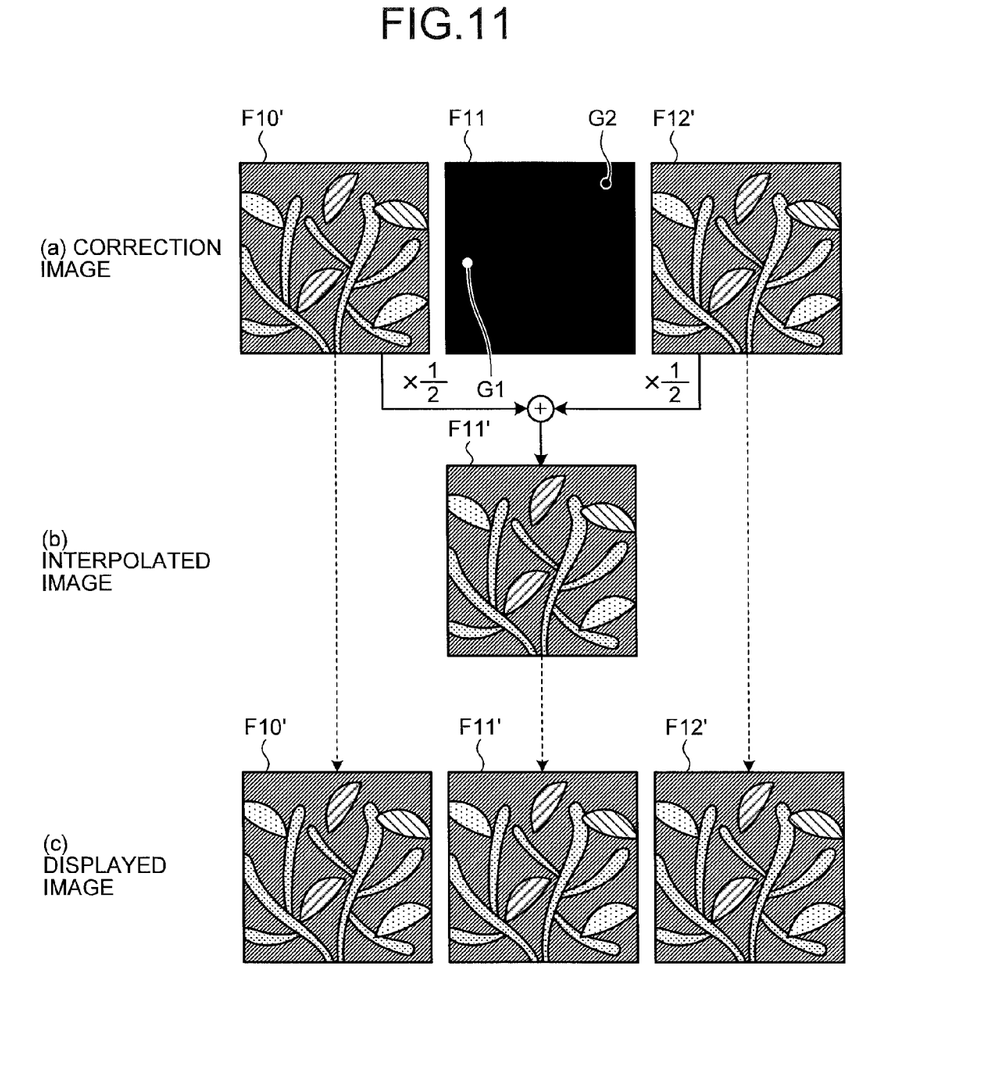
FIG. 11 is a diagram schematically describing an outline of an interpolation method in which an image is interpolated by an image interpolation unit of the endoscope system according to the second embodiment of the present invention.

In Step S213, in the case where the normal exposure image data received from the pixel correction unit 561 corresponds to a frame of the dark image data (Step S213: Yes), the image interpolation unit 562 interpolates a normal exposure image data corresponding to the frame of the dark image data based on the most recent normal exposure image data and the current normal exposure image data (Step S214). More specifically, as illustrated in FIG. 11(a), in the case where the normal exposure image data received from the pixel correction unit 561 corresponds to the frame F11 of the dark image data, the image interpolation unit 562 interpolates a normal exposure image F11' corresponding to the frame of the dark image data by: multiplying a predetermined coefficient such as 0.5 by a most recent normal exposure image F10' corresponding to most recent normal exposure image data and a current normal exposure image F12' corresponding to current normal exposure image data; and combining the images (FIG. 11(a)→FIG. 11(b)).

Subsequently, the image interpolation unit 562 outputs, as display image data, the normal exposure image data of the frame F11' for the dark image data to the display device 4 (Step S215). This prevents frame drop in the image data generated by the image sensor 244. Therefore, an in-vivo image inside the body cavity of the subject can be displayed smoothly. After Step S215, the endoscope system 1a proceeds to Step S216.

Step S216 corresponds to Step S113 in FIG. 3 described above.

In Step S213, in the case where the normal exposure image data received from the pixel correction unit 561 does not correspond to the frame of the dark image data (Step S213: No), the endoscope system 1a proceeds to Step S216.

According to the above-described second embodiment of the present invention, high-resolution image can be displayed because a blinking defective pixel in the image sensor 244 can be surely corrected.

Further, according to the second embodiment of the present invention, the dark reference image data is generated at the time of examining the subject. Therefore, even in the case where any blinking defective pixel is generated at the time of examination or during examination, the blinking defective pixel can be surely detected and corrected.

In the second embodiment of the present invention, the dark reference image data recorded in the dark reference image data recording unit 542 may be deleted when examination of the subject is finished. This can prevent memory capacity of the recording unit 54 of the processing device 5a from increasing in size.

Other Embodiments

In the present invention, an illumination controller turns off a light source unit in synchronization with a frame rate of an image sensor, but a frame (frame time) of a lights-out period during which the light source unit is turned off may be equal to or longer than a frame of a lighting period during which the light source unit is turned on (equal to or longer than the frame time of the lights-out period), and further a frame time of an exposure time (imaging time) of the image sensor during the lights-out time may be set to equal to or longer than exposure time of the image sensor at the lighting time. Since this extends a light receiving time of each pixel in the image sensor, a blinking defective pixel can be surely detected. Needless to mention, a frame time of the lights-out period during which the light source unit is turned off may be set longer than the frame time of the lighting period during which the light source unit is turned on, and further the frame time of the exposure time (imaging time) of the image sensor during the lights-out time may also be set longer than the exposure time of the image sensor at the lighting time.

In the above-described embodiments, an example of an endoscopic device that can be inserted into a subject has been described, but the present invention is also applicable to a capsule endoscope in which an image sensor, a light source device, and a processing device are provided in a capsule-shaped casing that can be inserted into the subject.

In the above-described embodiments, the image sensor is configured to generate dark image data by lighting off a light source under control of the illumination controller, but the light source device may also be turned off by, for example: providing a rotary filter including a light shielding area on an optical path of a light source; and rotating the rotary filter.

In the above-described embodiments, a pixel correction unit corrects a blinking defective pixel in real time, but image data consecutively generated by the image sensor may be recorded in a recording medium and a blinking defective pixel may be corrected at the time of reproducing the image data recorded in the recording medium.

According to some embodiments, it is possible to surely detect and correct a blinking defective pixel in an image sensor.

In the description for the flowcharts in the present specification, the wording such as "first", "after that", and "subsequently" are used to clarify anteroposterior relations in the processing between Steps, but note that the processing order required to implement the present invention is not uniquely determined by the wording. In other words, the processing order illustrated in the flowcharts of the present specification can be changed within a range having no contradiction.

Thus, the present invention may include various embodiments not recited herein, and various kinds of design change and the like can be made within a technical idea specified in the scope of claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   a light source unit configured to emit illumination light to illuminate a subject;
   an image sensor having a plurality of pixels arranged two-dimensionally, each of the plurality of pixels being configured to receive light and perform photoelectric conversion on the received light to output an electric signal, and the image sensor being configured to image the subject at a predetermined frame rate and generate image data of the subject;
   an illumination controller configured to turn off the light source unit in a predetermined cycle;
   a difference calculation unit configured to calculate, for each pixel, difference data between a dark image and a dark reference image, the dark image being output from the image sensor during lights-out time when the illumination controller turns off the light source unit, and the dark reference image having been obtained by averaging a plurality of dark images generated by the image sensor and having been preliminarily recorded;
   a blinking defective pixel detection unit configured to determine, for each pixel of the difference data calculated by the difference calculation unit, whether a pixel value is a predetermined threshold value or more, and to detect a pixel whose pixel value is the predetermined threshold value or more, as a blinking defective pixel in the image sensor;
   an image output timing adjustment unit configured to temporarily hold the image data generated by the image sensor, and to output the image data at predetermined timing; and
   a pixel correction unit configured to correct the electric signal output from the blinking defective pixel detected by the blinking defective pixel detection unit in the image data output by the image output timing adjustment unit, by using electric signals output from neighboring pixels of the blinking defective pixel, and to output the image data to a display device,
   wherein
   if the illumination controller turns off the light source unit n times (n≥1) per unit time and the predetermined frame rate is set to N, the illumination controller is configured to turn off the light source unit such that the lights-out time of the light source unit per frame is 1/N, and
   the image output timing adjustment unit is configured to output the image data at a frame rate of N−n.

2. The endoscope system according to claim 1, wherein the illumination controller is configured to turn off the light source unit in a first frame per unit time.

3. The endoscope system according to claim 1, wherein the illumination controller is configured to set the number of frames of a lights-out period during which the light source unit is turned off, to be equal to or larger than the number of frames of a lighting period during which the light source unit is turned on.

4. The endoscope system according to claim 1, wherein the light source unit includes an LED light source.

5. The endoscope system according to claim 1, wherein the dark reference image is obtained by averaging the plurality of dark images subsequently generated by the image sensor at the time of shipping the endoscope system or at the time of examination in which the endoscope system is inserted into a body cavity of the subject in use.

6. The endoscope system according to claim 1, further comprising a capsule-shaped casing configured to be inserted into a body cavity of the subject,
   wherein the light source unit, the image sensor, the illumination controller, the difference calculation unit, the blinking defective pixel detection unit, and the pixel correction unit are provided inside the casing.

7. A pixel correction method executed by an endoscope system, the endoscope system comprising: a light source unit configured to emit illumination light to illuminate a subject; and an image sensor having a plurality of pixels arranged two-dimensionally, each of the plurality of pixels being configured to receive light and perform photoelectric conversion on the received light to output an electric signal, the method comprising:
   turning off the light source unit in a predetermined cycle;
   causing the image sensor to perform imaging during lights-out time when the light source unit is turned off to generate a dark image;
   calculating, for each pixel, difference data between the dark image and a dark reference image, the dark reference image having been obtained by averaging a plurality of dark images generated by the image sensor and having been preliminarily recorded;
   determining, for each pixel of the difference data, whether a pixel value is a predetermined threshold value or more, and detecting a pixel whose pixel value is the predetermined threshold value or more, as a blinking defective pixel in the image sensor;

causing the image sensor to image the subject at a predetermined frame rate to generate image data of the subject;

temporarily holding the image data, and outputting the image data at predetermined timing; and correcting the electric signal output from the blinking defective pixel in the image data output at the predetermined timing, by using electric signals output from neighboring pixels of the blinking defective pixel, and outputting the image data to a display device, wherein if the light source unit is turned off n times (n≥1) per unit time and the predetermined frame rate is set to N, the light source unit is turned off such that the lights-out time of the light source unit per frame is 1/N, and the image data is output at a frame rate of N−n.

* * * * *